(12) United States Patent
Gleich et al.

(10) Patent No.: US 6,861,449 B2
(45) Date of Patent: Mar. 1, 2005

(54) METHOD OF TREATING NEUTROPHIL-RELATED DISEASES WITH TOPICAL ANESTHETICS

(75) Inventors: Gerald J. Gleich, Salt Lake City, UT (US); Loren W. Hunt, Jr., Athens, GA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/326,224

(22) Filed: Dec. 20, 2002

(65) Prior Publication Data

US 2003/0171402 A1 Sep. 11, 2003

Related U.S. Application Data

(63) Continuation of application No. PCT/US01/19977, filed on Jun. 22, 2001.
(60) Provisional application No. 60/214,031, filed on Jun. 23, 2000.

(51) Int. Cl.[7] .............................................. A61K 31/24
(52) U.S. Cl. ....................................... 514/535; 514/851
(58) Field of Search .................................. 514/535, 851

(56) References Cited

U.S. PATENT DOCUMENTS 5,510,339 A * 4/1996 Gleich et al. ............... 514/171
5,631,267 A    5/1997 Gleich et al. ............... 514/312

FOREIGN PATENT DOCUMENTS

| WO | WO-92/14466 | 9/1992  | ......... A61K/31/485 |
| WO | WO-99/63985 | 12/1999 | ......... A61K/31/165 |

OTHER PUBLICATIONS

Abrosimov, V. N., "Inhalation of Lidocaine in Pulmonology", *Klinicheskaya Meditsina (Moscow)*, vol. 66, No. 12, (1988), pp. 57–59.

Krasnowska, Maryla, et al., "Application of Lidocaine Inhalation in Chronic Bronchitis", *Pneumonologia Polska*, vol. 54, No. 4, (1986), pp. 144–147.

Abrosimov, V..N. ,"Lidocaine Inhalations in pulmonary diseases", *Biosciences Information Service, Accession No. PREV198988077919, XP002191618*, (1988).

Krasnowska, M..,et al. ,"The use of lidocaine inhalation in Chronic bronchitis", *XP002191619 & Pneumonologia Polska*, vol. 54, No. 4 (Poland), (1986), 144–147.

* cited by examiner

*Primary Examiner*—Kevin E. Weddington
(74) *Attorney, Agent, or Firm*—Schwegman, Lundberg, Woessner & Kluth, P.A.

(57) ABSTRACT

A therapeutic method is provided to treat neutrophil-associated pulmonary diseases, such as chronic obstructive pulmonary disease, by locally administering to a mammal in need of such treatment, an effective amount of a topical anesthetic, such as lidocaine, or a pharmaceutically acceptable salt thereof.

9 Claims, 4 Drawing Sheets

METHOD OF TREATING NEUTROPHIL-RELATED DISEASES WITH TOPICAL ANESTHETICS

RELATED APPLICATION

This application is a continuation under 35 U.S.C. 111(a) of International Application No. PCT/US01/19977 filed Jun. 22, 2001 and published in English as WO 02/00218 A2 on Jan. 3, 2002, which claimed priority from U.S. Provisional Application Ser. No. 60/214,031 filed Jun. 23, 2000, which applications and publications are incorporated herein by reference.

BACKGROUND OF THE INVENTION

There are several neutrophil-associated pulmonary diseases, including chronic obstructive pulmonary disease (COPD), chronic bronchitis (CB), pulmonary emphysema, α-1 anti-trypsin deficiency, cystic fibrosis, idiopathic pulmonary fibrosis, and adult respiratory distress syndrome.

In chronic bronchitis there is cough and mucous hypersecretion with enlargement of tracheobronchial submucosal glands and a disproportionate increase of mucous acini. CD8+ve lymphocytes predominate over CD4+ve cells and there are increased numbers of subepithelial macrophages and intra-epithelial neutrophils. Exacerbations of bronchitis are associated with a tissue eosinophilia, apparent absence of IL-5 protein but gene expression for IL-4 and IL-5 is present. In small or peripheral airways disease, there is inflammation of bronchioli and mucous metaplasia and hyperplasia, with increased intraluminal mucus, increased wall muscle, fibrosis, and airway stenoses (also referred to as chronic obstructive bronchiolitis). Respiratory bronchiolitis involving increased numbers of pigmented macrophages is a critically important early lesion. Increasingly severe peribronchiolitis includes infiltration of T lymphocytes in which the CD8+ subset again predominates. These inflammatory changes may predispose to the development of centrilobular emphysema and reduced FEV1 via the destruction of alveolar attachments.

In emphysema there is abnormal, permanent enlargement of airspaces distal to the terminal bronchiolus (i.e. within the acinus) accompanied by destruction of alveolar walls and without obvious fibrosis. The severity of emphysema, rather than type, appears to be the most important determinant of chronic deterioration of airflow, and in this there may be significant loss of elastic recoil and microscopic emphysema prior to the observed macroscopic destruction of the acinus. Airway obstruction and chronic expectoration, as well as accelerated decline in lung function, are associated with increased numbers of neutrophils in the sputum of smokers and ex-smokers.

COPD is a complex condition with an imprecise definition, which makes a definitive morphological description difficult. Chronic bronchitis and COPD are caused by a predominantly neutrophilic bronchial inflammation with sputum production and periodic flares of increased cough and sputum volume, often associated with shortness of breath. COPD generally refers to those patients that have associated parenchymal emphysematous changes with loss of lung compliance, increased air trapping, and reduced expired lung volumes and expiratory flow rates. It is believed that emphysematous changes are also the result of neutrophil-induced parenchymal damage. Barnes, P. J. *Chest* 117:10S014S (2000). Neutrophils are present in large numbers in bronchoalveolar lavage and in sputum of patients with chronic bronchitis and COPD, and sputum neutrophils correlate inversely to the FEV1 in patients with COPD. Yamamoto, C. et al., *Chest* 112:505–510 (1997); Peleman, R. A. et al., *Eur. Resp. Journal* 13:839–843 (1999). Interleukin-8 (IL-8) is believed to play a primary role in this activation. Peleman, R. A. et al., *Eur. Resp. Journal* 13:839–843 (1999); Pesci, A. et al., *Respiratory Medicine* 92:863–870 (1998).

IL-8 is a chemoattractant and granule release stimulus for neutrophils. Increased concentrations of IL-8 are found in the sputum and bronchoalveolar lavage fluids of patients with COPD and chronic bronchitis, and these concentrations correlate with the number of neutrophils recovered. Bronchoalveolar lavage fluid IL-8 concentrations are higher in cigarette smokers than in nonsmokers, and cigarette smoke concentrate induces IL-8 release from cultured human bronchial epithelial cells. "Cigarette Smoke Induces Interleukin-8 Release from Human Bronchial Epithelial Cells," *Am. J Respir. Crit. Care Med.*, 155:1770 (1990). Nicotine prolongs neutrophil survival by suppressing apoptosis. Aoshiba, K. et al., *J. Lab Clin. Med.* 127:186–194 (1996).

The role of glucocorticoids in the treatment of COPD is controversial. As opposed to the eosinophilic inflammation of asthma, this type of inflammation is relatively glucocorticoid resistant when treated with either systemic or topical glucocorticoids. Studies have shown that inhaled steroids have little anti-inflammatory effect, and that the inflammatory process in COPD is resistant to the anti-inflammatory effect on glucocorticoids. Barnes P. J., *Am J. Resp. & Critical Care Med.* 160:S72–9 (1999); Keatings, V. M et al., *Am J. Resp. & Critical Care Med.* 155:542–548 (1997); Culpitt S. V., et al., *Am J. Resp. & Critical Care Med.* 160:1635–1639 (1999). Furthermore, studies have shown that glucocorticoids have no effect on the long-term decline of pulmonary function in patients with COPD. Vestbo, J. et al., *Lancet* 353:1819–1823 (1999). Sputum IL-8 concentrations correlate with long-term decline of pulmonary function in COPD, and glucocorticoid treatment in these patients does not result in reduction of neutrophils or IL-8, even in those patients with COPD who have eosinophils in their sputum. It has been recently shown that some patients with severe asthma have only neutrophils in their sputum, and these patients do not respond to glucocorticoids. At this time, there is no effective anti-inflammatory therapy for these patients.

Other than smoking cessation, there is no established treatment for the neutrophilic inflammation in chronic bronchitis and COPD, nor the progressive pulmonary function decline in patients with COPD. Because the majority of these patients have smoking as an etiologic factor in their disease, smoking cessation has been the only preferred treatment. Hurd, S. et al., *Chest* 117:1S–4S (2000). Unfortunately, smoking cessation is not a realistic therapeutic remedy in the vast number of patients effected. Despite many different types of intervention programs for nicotine dependence, the long-term abstinence rate for smokers is only about 20–25%. This means that over three fourths of these patients (about 25% of the US adult population) continue to smoke and develop neutrophilic airway inflammation, and risk sustaining variable degrees of progressive airway and parenchymal damage. Furthermore, smoking cessation may take years to accomplish or not be possible at all for most patients who smoke. Finally, there is evidence that in some patients, especially those with COPD, that there can be ongoing neutrophilic airway inflammation that continues after smoking cessation. Rutgers, S. R. et al., *Thorax* 55:12–18 (2000); Maziak, W. et al., *Am. J. Resp.*

Crit. Care Med. 157:998–1002 (1998); Turato, G. et al., Am. J. Resp. Crit. Care Med. 152:1262–1267 (1995).

Pulmonary emphysema is defined as an abnormal, permanent enlargement of the air spaces distal to the terminal bronchioles with destruction of the air space walls, but without obvious fibrosis. Central to the pathogenesis of emphysema is lung destruction resulting from inadequate protection of the alveoli against enzymes released by inflammatory cells. The proteolytic enzymes implicated in the development of emphysema include neutrophil elastase, a major serine protease contained within neutrophil granules.

In $\alpha_1$-Antitrypsin Deficiency disease, there is a deficiency of the protein neutralizing neutrophil elastase, namely $\alpha_1$-antitrypsin. Moreover, there is evidence that the numbers of neutrophils migrating into the lung parenchyma is increased. Because of the inadequate defenses against neutrophil elastase, uninhibited neutrophil elastase is free to interact with substrates and inflammatory cells activating them. The result of this process is proteolytic destruction by neutrophil elastase of the fragile alveolar walls culminating in a gradual destruction of alveoli. This process is strikingly accelerated in cigarette smokers.

Cystic fibrosis is a common hereditary disorder of Caucasians and represents the most aggressive form of bronchitis known. Respiratory manifestations of cystic fibrosis develop at an early age, even in the first year of life. Frequent respiratory infections occur with production of thick, sticky sputum. The clinical course is punctuated by acute exacerbations of inflammation and infection of the airways with progressive deterioration of airway function. The pulmonary inflammation typical of cystic fibrosis resembles that of $\alpha_1$-antitrypsin deficiency and the epithelial surface of the lung in both disorders is burdened by neutrophil elastase and oxidants. However, in cystic fibrosis the bronchial inflammation is much more intense and the numbers of neutrophils in the airway epithelial lining fluid may be 500 times greater than in normal individuals. Although the pathogenesis of airway inflammation in patients with cystic fibrosis remains the subject of debate, nonetheless neutrophil elastase is implicated as playing a critical role. In cystic fibrosis, the normal protective defenses against proteases are intact, but the inflammation on the airway epithelial surface is so intense that these defenses against neutrophil elastase are overwhelmed and rendered ineffective.

The bronchitis associated with cystic fibrosis is the most aggressive form of bronchitis known, but the bronchitis associated with cigarette smoking is by far the most common. The population of inflammatory cells includes increased numbers of neutrophils, and they release an increased burden of oxidants and proteases including neutrophil elastase on the airway epithelial surface. Here, as in cystic fibrosis, it is assumed that the defenses of the airway against proteases are overwhelmed by the inflammation, albeit not to the extent as in cystic fibrosis.

The etiology of idiopathic pulmonary fibrosis is unknown, however, evidence exists that these patients show an inflamed lower respiratory tract even before the development of frank fibrosis. Among the inflammatory cells, neutrophils are prominent. It is believed that activated inflammatory cells damage alveolar structures by releasing oxidants and proteases, and that these reactants play a major role in injury to the epithelium and endothelium in idiopathic pulmonary fibrosis.

Considerable evidence links inflammation to the pathology of Acute (Adult) Respiratory Distress Syndrome (ARDS). Moreover, the neutrophil, in particular, with its extensive armamentarium of toxins, which can injure and destroy host tissue, has been implicated as an important mediator of ARDS.

Therefore, there is a driving need to develop new and effective treatments for neutrophil-associated pulmonary diseases such as COPD, CB, pulmonary emphysema, α-1 anti-trypsin deficiency, cystic fibrosis, idiopathic pulmonary fibrosis, and adult respiratory distress syndrome.

SUMMARY OF THE INVENTION

The present invention provides a method for treating a neutrophil-associated pulmonary disease by locally administering to the respiratory tract of an afflicted human an amount of a therapeutic preparation containing a topical anesthetic effective to counteract the symptoms of the disease. The therapeutic preparation may be administered in combination with a pharmaceutically acceptable liquid vehicle, and may be administered by spraying or by nebulization. The topical anesthetic of the therapeutic preparation may be administered at a daily dose of about 2.0–15 m/kg. The neutrophil-associated pulmonary disease to be treated by the present invention may be chronic obstructive pulmonary disease (COPD), chronic bronchitis (CB), cystic fibrosis, α-1 anti-trypsin deficiency, pulmonary emphysema, adult respiratory distress syndrome, or idiopathic pulmonary fibrosis.

The topical anesthetic may be bupivacaine, dibucaine, an N-arylamide, an ester between a carboxylic acid of the general formula:

wherein Ar is $C_6H_3$ and each $R^2$ and $R^3$ is H, halo, $(R^1)(H)N$—, wherein $R^1$ is $(C_1-C_5)$alkyl, $H_2N$—, or $(C_2-C_5)$alkoxy; and an alcohol of the general formula:

wherein X is a $(C_1-C_5)$ branched-or straight-chain alkylene; $R^4$ is H or $(C_1-C_4)$alkyl, $R^5$ is $(C_1-C_4)$alkyl, or $R^4$ and $R^5$ taken together can be a 5- or 6-membered heterocycloalkiphatic ring, optionally substituted by $(C_1-C_3)$alkyl or having an additional ring O- or N-atom; or a pharmaceutically acceptable salt thereof. In one embodiment, the topical anesthetic may be an N—$(C_7-C_{22})$arylamide of an amino-substituted $(C_1-C_5)$carboxylic acid or a pharmaceutically acceptable salt thereof. Alternatively, the topical anesthetic may be an N-[(mono- or di-$(C_1-C_4)$alkyl)phenyl]amide of an aliphatic $(C_1-C_5)$carboxylic acid, wherein said acid is substituted with $(R)(R')N$—, wherein R is H or $(C_1-C_5)$alkyl and R' is $(C_1-C_5)$alkyl; or a pharmaceutically acceptable salt thereof. In particular, the topical anesthetic may be lidocaine, prilocaine, etidocaine, or a pharmaceutically acceptable salt thereof. Further, the topical anesthetic may be an aminoalkylbenzoate or a pharmaceutically acceptable salt thereof. The topical anesthetic may be procaine, chloroprocaine, dyclonine, tetracaine, benoxinate, proparacaine, meprylcaine, piperocaine or a pharmaceutically acceptable salt thereof.

DETAILED DESCRIPTION OF THE INVENTION

Figure 1:
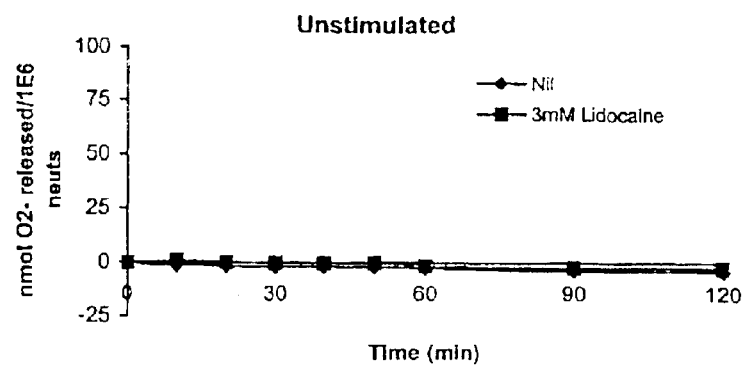
FIG. 1 is a graphical depiction of the time course of superoxide anion production by unstimulated neutrophils in the presence and absence of 3 mM lidocaine. Note that no superoxide anion is produced by the unstimulated neutrophils.

The term "treatment" as used herein includes any treatment of a condition or disease in a human, and includes inhibiting the disease or condition, (i.e. arresting its development), relieving the disease or condition (i.e. causing regression of the condition), or relieving the conditions caused by the disease (i.e. symptoms of the disease).

The term "therapeutically effective amount" refers to that amount which is sufficient to effect treatment, as defined herein, when administered to a human in need of such treatment. The therapeutically effective amount will vary depending on the subject and disease state being treated, the severity of the affliction and the manner of administration, and may be determined routinely by one of ordinary skill in the art.

Topical Anesthetics

Topical anesthetics, all of which are believed to be useful in the present invention, are an art-recognized class of drugs which temporarily interrupt mammalian nerve transmissions. They can generally be grouped into two chemical classifications structurally; the N-arylamides or carboxamides, such as lidocaine; and the aminoalkylbenzoates, such as procaine, benoxinate and proparacaine. Preferred N-aryl amides are N—($C_7$–$C_{22}$) arylamides of amino-substituted ($C_1$–$C_5$)carboxylic acids, e.g., N-[(mono-or di-($C_1$–$C_4$)alkyl)phenyl]amides of aliphatic ($C_1$–$C_5$)carboxylic acids, which acids are preferably substituted with the moiety (R)($R^1$)N— wherein R and $R^1$ are each ($C_1$–$C_5$)alkyl. For example, a preferred carboxylic acid can have the general formula (R)($R^1$)N(X)$CO_2$H wherein R and $R^1$ are as defined above and X is a branched- or straight-chain ($C_1$–$C_5$)alkylene group such as 1,1-ethylene, 1,2-ethylene, methylene, 2,2-propylene, 1,3-propylene, and the like. Another preferred class of N-arylamides are the N-[(mono-or di-($C_1$–$C_4$)alkyl)phenyl] amides of 5- or 6-membered-heterocycloaliphatic carboxylic acids, which acids have one or two [($C_1$–$C_4$)alkyl-substituted]N atoms, i.e., N-butylpiperidine-2-carboxylic acid.

The aminoalkylbenzoates include esters between benzoic acids and alcohols of the general formula ($R^4$)($R^5$)—N(X)OH, wherein X is as defined above, $R^4$ is H or ($C_1$–$C_4$)-alkyl, $R^5$ is ($C_1$–$C_4$)alkyl or $R^4$ and $R^5$ taken together are a 5- or 6-membered heterocycloaliphatic ring, optionally substituted by ($C_1$–$C_3$)alkyl or having an additional ring O- or N-atom. The benzoic acid moiety can be the moiety ($R^2$)($R^3$)Ar$CO_2$H wherein Ar is an aromatic —$C_6H_3$— radical or "phenylene" and (phenylene) and each $R^2$ and $R^3$ is H, halo, preferably $C_1$, ($R^5$)(H)N—, $H_2$N— or ($C_1$–$C_5$)alkoxy.

Useful topical anesthetics include lidocaine ((2-diethylamino)-N-(2,6-dimethylphenyl)acetamide) (see Lofgren et al. (U.S. Pat. No. 2,441,498), May & Baker (British Patent No. 706409) and J. F. Macfarlane & Co. (British Patent No. 758,224)); bupivacaine (1-butyl-N-(2,6-dimethylphenyl)-2-piperidinecarboxyamide) (see Thuresson et al., (U.S. Pat. No. 2,955,111) and Sterling Drug (British Patent Nos. 1,166,802 and 1,180,712)); mepivacaine (2-piperidinecarboxyamide, -(2,6-dimethylphenyl)-1-methyl), chloroprocaine (4-amino-2-chlorobenzoic acid 2-(diethylamino)ethyl ester); procaine (4-aminobenzoic acid 2-(diethylamino)ethyl ester); etidocaine (N-(2,6-dimethylphenyl)-2-(ethylpropylamino)butanamide; see, Astra (German Patent No. 2162744)); tetracaine (4-(butylamino)benzoic acid 2-(dimethylaminoethyl ester; see Shupe (U.S. Pat. No. 3,272,700)); benoxinate (4-amino-3-butoxybenzoic acid 2-(diethylamino)ethyl ester (U.K. Patent No. 654,484)); proparacaine (3-amino-4-propoxybenzoic acid 2-(diethylamino)ethyl ester); dibucaine (3-butoxy-N-[2-(diethylamino)ethyl]-4-quinolinecarboxyamide; Miescher (U.S. Pat. No. 1,825,623)); dyclonine (1-(4-butoxyphenyl)-3-(1-piperidinyl-1-propanone)); isobucaine (1-propanol, 2-methyl-2-[(2-methylpropyl)amino]benzoate; meprylcaine ([(2-methyl)(2-propylamino)propyl]benzoate); piperocaine ((2-methylpiperidin-1-ylpropyl(benzoate)); prilocaine (N-(2-methylphenyl)-2-(propylamino) propanamide); propoxycaine (2-(diethylamino)ethyl-([2'-methyl-4'-amino]benzoate)); pyrrocaine (1-(pyrrolidin-1-yl)-N-(2,6-dimethylphenyl)acetamide; butacaine (((3-dibutylamino)propyl)-(2'-amionobenzoate)); cyclomethylcaine (((3-(2'-methylproperidine-1-yl))propyl) [4'-cyclohexyloxy-benzoate]); dimethyisoquin, diperodon, hexylcaine ((([(2-cyclohexylamino)(1-methyl)]ethyl) (benzoate); proparacaine (((2-diethylamino)ethyl) [(4'-propyloxyl-3'-amino)benzoate]); cocaine and its analogs (see, F. I. Carroll et al., J. Med. Chem., 34, 2719 (1991); Eur. J. Pharmacol., 1.84, 329 (1990); and the pharmaceutically acceptable salts thereof. Preferred salts include the amine addition salts of inorganic and organic acids, e.g., the hydrochloride, hydrobromide, sulfate, oxalate, fumarate, citrate, malate, propionate and phosphate salts. The hydrochloride and sulfate salts are preferred for use in the present invention.

These topical anesthetics and the salts thereof are discussed in detail in Remington's Pharmaceutical Sciences, A. Osol, ed., Mack Pub. Co., Easton, Pa. (16th ed. 1980), and in The Merck Index (11th ed. 1989).

Administration and Dosages

While it is possible that, for use in therapy, the topical anesthetics or their salts may be administered as the pure dry chemicals, as by inhalation of a fine powder via an insufflator, it is preferable to present the active ingredient as a pharmaceutical formulation. The invention thus further provides a pharmaceutical formulation having one or more topical anesthetics, or pharmaceutically acceptable salts thereof, together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for administration by inhalation or insufflation or for nasal, intraocular or other topical (including buccal and sub-lingual) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both.

For administration to the upper (nasal) or lower respiratory tract by inhalation, the compounds according to the invention are conveniently delivered from an insufflator, nebulizer or a pressurized pack or other convenient means of delivering an aerosol spray. Pressurized packs may have a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges. Alternatively, it may be provided in gelatin or blister packs from which the powder may be administered with the aid of an inhalator, insufflator or a metered-dose inhaler.

For intra-nasal administration, the compounds of the invention may be administered via nose drops, a liquid spray, such as via a plastic bottle atomizer or metered-dose inhaler. Typical of atomizers are the Mistometer (Wintrop) and the Medihaler (Riker).

Drops, such as eye drops or nose drops, may be formulated with an aqueousor non-aqueous base also having one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

For topical administration to the eye, nasal membranes or to the skin, the compounds according to the invention may be formulated as ointments, creams or lotions, or as a transdermal patch or intraocular insert. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth or throat include lozenges having active ingredient in a flavored base, usually sucrose and acacia or tragacanth; pastilles having the active ingredient in an inert base such as gelatin and glycerin or sucrose and acacia; and mouthwashes having the active ingredient in a suitable liquid carrier.

When desired, the above-described formulations adapted to give sustained release of the active ingredient may be employed, e.g., by combination with certain hydrophilic polymer matrices. The pharmaceutical compositions according to the invention may also contain other active ingredients such as antimicrobial agents, or preservatives. The compounds of the invention may also be used in combination with other therapeutic agents, such as bronchodilators or anti-inflammatory agents.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician. In general, however, a suitable unit dose for counter-acting respiratory tract symptomology will deliver from about 0.05 to about 10–15 mg/kg, e.g., from about 0.10 to about 5.0 mg/kg of body weight per day.

The desired dose may conveniently be presented in a single dose or as divided doses administered at appropriate intervals, for example, as two, three, four or more sub-doses per day. The sub-dose itself may be further divided, e.g. into a number of discrete loosely spaced administrations; such as multiple inhalations from an insufflator or by application of a plurality of drops into the eye or nose.

The invention will be further described by reference to the following detailed Examples.

EXAMPLE 1

Inhibition of Neutrophil Superoxide Production by Lidocaine

Lidocaine has an inhibitory effect on neutrophil superoxide production. Neutrophils were purified from heparinized venous blood of normal volunteers by sedimentation through a cushion of 1.085 gm/ml Percoll made in PIPES buffer, pH 7.4, supplemented with 50 mM NaCl, 5 mM KCl, 25 mM NaOH, and 5.4 mM glucose) and centrifuged at 2,000 rmp in a Beckman CS-6KR centrifuge for 30 minutes with no brake. Plasma, mononuclear cells, and Percoll layers were removed and the erythrocytes were lysed by osmotic shock. The remaining pellet, which was ~90% neutrophils, was used in the experiment.

Figure 2:
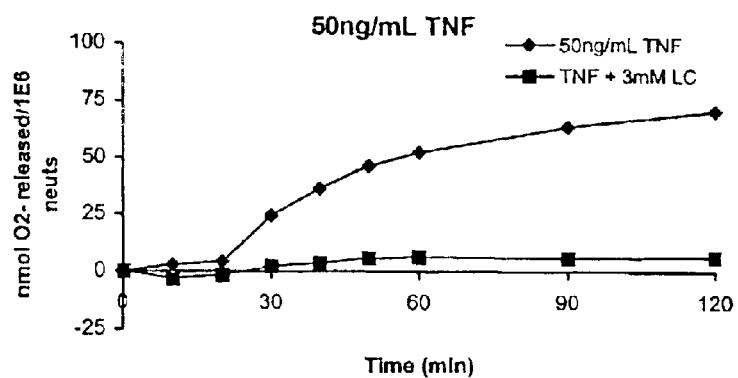
FIG. 2 is a graphical depiction of the effect of tumor necrosis factor (TNF) on neutrophils. Note that in the presence of TNF-α, considerable superoxide anion is released from the neutrophil by 30 minutes and still resides at 120 minutes. In contrast, 3 mM lidocaine, virtually totally suppresses the TNF-α stimulated neutrophils superoxide anion production.
Figure 3:
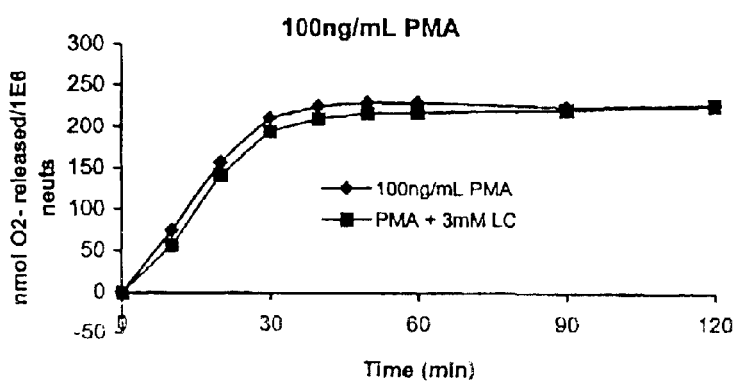
FIG. 3 is a graphical depiction of the effect of phorbol-myristate acetate (PMA) on neutrophil superoxide anion production. The results show that PMA stimulates superoxide anion very considerably, but that lidocaine does not alter this production. The inability of lidocaine to alter PMA stimulate superoxide anion production indicates that lidocaine is not toxic to the neutrophil.

The superoxide production was measured using cytochrome c reduction in a plate assay at a concentration of 50,000 neutrophils/well and was done in duplicate. There was no superoxide release in the absence of stimulus; TNF-alpha induced superoxide release was almost totally inhibited by 3 mM lidocaine, but PMA induced superoxide production was not inhibited by lidocaine. See FIGS. 1–3.

EXAMPLE 2

Case Report of Patient with Bronchitis Treated with Lidocaine Inhalation

The patient was a 36-year-old female first seen in 1996 with a six month history of harsh cough affecting her both during the night and the day. Copious (about 50 ml per day), thick, yellow to white sputum was produced. She was often awakened at night with chest heaviness and dyspnea. Albuterol treatment reduced the cough and minimally alleviated the chest tightness. The patient was treated with prednisone and antibiotics on two occasions and this treatment. improved her symptoms, but did not eliminate the sputum production. The patient worked as a scrub nurse in an operating room, but she did not note any worsening of her symptoms while at work or at home. When initially evaluated, the patient was receiving prednisone, 30 mg every other day, Salmeterol twice daily and Asthmacort four inhalations four times a day. Two sputum examinations revealed a striking infiltration with neutrophilic leukocytes.

The patient's past medical history was relevant in that in 1993 she had the onset and diagnosis of chronic ulcerative colitis. Her symptoms were severe and difficult to control despite the use of prednisone, Asulfadine and glucocorticoid enemas. In 1995 she underwent a subtotal colectomy and the pathology was consistent with severe ulcerative colitis.

Physical examination was unremarkable save for bilateral rhonchi and scattered wheezes. She did have an ileostomy with a stump and pouch inflammation.

Laboratory evaluation was unremarkable save for the presence of a diffusing capacity for carbon monoxide which was at the borderline between normal and abnormally low and a flow volume contour which was believed to indicate mild pulmonary obstruction. Skin tests for inhalant allergens were positive to several inhalants and allergens.

The patient was treated with lidocaine by inhalation, the prednisone was reduced and subsequently stopped and the other medications were stopped. While under lidocaine therapy, her sputum volume and cough diminished strikingly over a span of three weeks. The patient continued lidocaine therapy for the following year and when interviewed in early 1998 reported continued improvement on a regimen of lidocaine by inhalation and occasional courses of antibiotics.

EXAMPLE 3

Treatment of Airway Neutrophilia in Chronic Bronchitis and COPD

In preliminary studies, it was discovered that lidocaine has potent anti-inflammatory properties with the ability, in vitro, to inhibit cytokine-stimulated eosinophilopoesis and prolongation of survival, activation, respiratory burst, and degranulation of eosinophils. Okada. S. et al., *J. Immunol.* 160:4010–4017 (1998). Subsequent in vivo studies have shown that lidocaine inhalation reduces or eliminates systemic glucocorticoids in most adult (Hunt, L. W. et al., *Mayo Clinic Proc.* 71:361–368 (1996)) and pediatric (Decco, M. L. et al., *Ann. Allergy Asthma Immunol.* 82:29–32 (1999)) patients with steroid-dependent asthma, and is able to replace topical glucocorticoids in patients with mild to moderate asthma. In the latter study, nebulized lidocaine also prevented the rise in peripheral blood eosinophils when topical glucocorticoids were withdrawn.

In vitro studies show that lidocaine inhibits depolarization of neutrophil membrane potential, superoxide generation and chemiluminescence response in neutrophils in a concentration-dependent manner. Tomoda, M. et al., *Masui-Japanese J. Anesthesiology* 41:369–375 (1992); Mikawa, K. et al., *Acta Anaesthesiologica Scandinavia* 41:524–528 (1997); Hattori, M. et al., *Anesthesia and Analgesia* 84:405–412 (1997). Inhibition of neutrophil aggregation and degranulation has also been shown. Hattori, M. et al., *Anesthesia and Analgesia* 84:405–412 (1997); Haines, K. A. et al., *J. of Immunology* 144:4757–4764 (1990). Lidocaine also inhibits activation of neutrophils by G-CSF (Ohsaka, A. et al., *Experimental Hematology* 22:460–466 (1994)), TNF-α (Kanbara, T. et al., *Biochemical Pharmacology* 45:1593–1598 (1993)), and GM-CSF. In animal models of neutrophil-mediated injury, lidocaine inhibits neutrophil tissue damage induced by hydrochloric acid (Nishina, K. et al., *Anesthesiology* 83:169–177 (1998)), reperfusion injury (Lamos, J. et al., *Arch Internationales De Pharmacodynamie et de Therapie* 331:179–188 (1996); Schmid, R. A. et al., *Annals of Thoracic Surgery* 61:949–955 (1996)), and endotoxin (Nishina, K. et al., *Anesthesiology* 83:169–177 (1995)).

Little human data is available on the effects of lidocaine on neutrophil-mediated lung disease. A patient with inflammatory bowel disease-associated severe bronchitis who had symptoms of copious sputum production (in excess of 150 ml/day), daily cough and chest tightness, and shortness of breath on exertion, who had not responded to topical or systemic glucocorticoids and multiple rounds of antibiotics over an 18 month period was treated. Lamos, J. et al., *Arch Internationales De Pharmacodynamie et de Therapie* 331:179–188 (1996). This patient had no eosinophils in the sputum, did not respond to bronchodilators, had no CT scan evidence of bronchiectasis, a negative methacholine challenge, and had never smoked. Within six weeks of starting nebulized lidocaine (100 mg four times daily), the sputum volume diminished to zero and the cough and chest tightness disappeared.

Methods

Aa randomized, single-blind, placebo-controlled study is conducted involving 50 patients with chronic bronchitis and COPD. The fifty patients are recruited over a two year period for study. Twenty-five subjects are treated with nebulized lidocaine (100 mg four times daily) and twenty five with nebulized saline over a 4 week period. Outcome variables include sputum total white and neutrophil count, sputum interleukin-8 (IL-8), peripheral blood neutrophil count, forced expiratory volume in one second (FEV1), weekly symptom score, and daily sputum volume. Additionally, all patients perform peak flow measurements and record their symptoms twice daily in diaries. All patients in the study are selected on the basis of being recent cigarette smokers who have stopped smoking within four weeks of study enrollment, and have a sputum total neutrophil cell count of $>5 \times 10^5$ cells.

50 patients, 18 to 75 years of age who have quit smoking within one month of entry into the study, with chronic bronchitis and COPD as defined by ATS criteria are selected and studied (Definition and Classification of Chronic Bronchitis, Asthma, and Pulmonary Emphysema: Statement by ATS Committee on Diagnostic Standards for Non-Tuberculous Respiratory Disease, *Am. Rev. Resp. Dis.*, 85, 762 (1962)). The patients have not been treated with either topical or systemic glucocorticoids, and have not had an acute respiratory infection for at least one month. Additionally, the patients maintain any present medications that they are taking for the duration of the study. All patients selected must have an initial sputum neutrophil cell count of equal or greater than $5.0 \times 10^5$ cells.

The patients are randomized on the basis of sex and similar pulmonary function values, and duration in weeks of smoking cessation. All subjects are asked to maintain smoking abstinence for the study duration and are issued symptom diaries and peak flow meters. After a one week "run-in" period, the subjects return to the clinic, have a review of their symptom diaries, and begin either placebo (2.5 cc or nebulized saline) or nebulized lidocaine (2.5 cc of 4% solution, or 100 mg, FDA IND #, 046891) four times daily for one month (see Study Design below). All patients have a physical examination, a CXR, complete blood count, serum cotinine, spirometry with bronchodilator, and sputum collection for sputum total and differential WBC and IL-8 measurement at the time of enrollment. All females of child bearing potential have a pregnancy test as part of their initial examination and are asked to continue their present method of contraception for the duration of the study. Subjects have a repeat sputum, CBC, serum cotinine, spirometry, and physical examination again at 4 weeks at the termination of the study. All patients complete daily symptom diaries and perform morning peak flow rates using a Wright mini-peak flow device.

Patient inclusion criteria are as follows: 1) age 18–75; 2) chronic bronchitis; 3) COPD; 4) former cigarette smoker who has recently stopped within four weeks; 5) the subject is willing to maintain smoking abstinence for the duration of the study period; 6) the subject is willing to complete daily diaries and complete other aspects of study participation, i.e., clinic visits, etc.; and 7) initial sputum total neutrophil count of at least $5.0 \times 10^5$ cells. (WBC counted/count volume×sputum volume×% sputum neutrophils)

Patient exclusion criteria are as follows: 1) an acute respiratory infection within 4 weeks; 2) the presence of any other chronic lung disease such as pulmonary fibrosis, chronic infectious process, hypersensitivity pneumonitis, bronchial asthma, bronchiectasis, sarcoidosis, or cystic fibrosis; 3) evidence or suspicion of oral pharyngeal, laryngeal, or lung cancer; 4) recent hemoptysis within 4 weeks; 5) a history of allergy to lidocaine; 6) pregnant or lactating females; 7) evidence of chronic cardiovascular or liver disease requiring regular medication; 8) a pre bronchodilator FEV1 of <40% of predicted; 9) using either topical or systemic glucocorticoid medication within the previous 4 weeks; 10) using potent anti-inflammatory medications such as immuran, methotrexate, cyclophosphamide, gold, anti-malarial, or any cancer chemotherapeutic agent within the previous 4 weeks; 11) having taken leukotriene modifying agents within the previous 2 weeks; and 12) having taken any immunomodfier agent such as Interferon gamma or alpha within the previous 2 months.

Study Design:

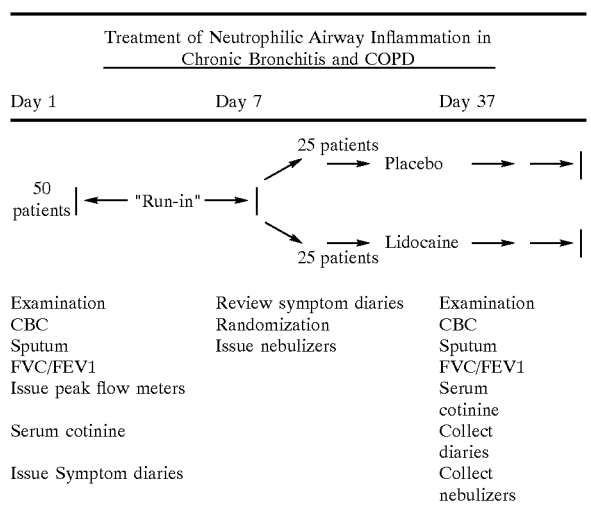

Treatment of Neutrophilic Airway Inflammation in Chronic Bronchitis and COPD

Sputum Induction and Analysis:

Analysis of induced sputum has been shown to be accurate, reproducible, noninvasive, and reflects the type and degree of lung airway inflammation. Yamamoto, C. et al., *Chest* 112:505–510 (1997); Peleman, R. A. et al., *Eur. Resp. Journal* 13:839–843 (1999); Gibson, P. G. et al., *Thorax* 44:693–699 (1989). Induction, collection, and processing of sputum is performed according to the method of Pin and Hargreave. Briefly, if the patient is unable to spontaneously produce a 5 cc sputum sample, sputum induction is performed using ultrasonically nebulized hypertonic saline administered in progressive 2 minute increments followed by attempts to cough and produce sputum. The nebulization continues until a total of 12 minutes have elapsed or the patient produces 5 cc of sputum. The initial specimen is collected in a 50 ml conical tube, vortexed and 1 cc of the sputum is aspirated and placed on ice for cytokine analysis. The remaining volume is weighed, and mixed with equal volumes of dithiothreitol, vortexed, then rocked for 15 min at 37° C. with frequent vortexing. The specimen is analyzed for total and differential cell counting.

Interleukin-8 Assay:

The untreated portion of the sputum, as described above, is mixed with an equal volume of normal saline, vortexed, and then centrifuged at $10^4 \times g$ for minutes. The supernatant is frozen at −70° C. for later analysis of IL-8. IL-8 is measured using a commercially available specific ELISA (R&D Systems Europe Ltd., Abingdon, UK).

Spirometric Pulmonary Function Testing:

FEV1 and FVC are obtained using the best of three efforts before and after albuterol bronchodilation using a MedGraphics Pulmonary Function Apparatus. Subjects perform efforts in a sitting position and spirometric methods are performed in accordance with American Thoracic Society criteria for acceptability and reproducibility. Standardization of Spirometry 1987 Update, *Am. Rev. Respir. Dis.*, 136, 1285 (1987).

Outcome Variables and Statistical Analysis:

The primary outcome variables are sputum total and neutrophil cell count, sputum IL-8 concentrations, sputum volume, symptom scores, peripheral blood total white and neutrophil counts, and FEV 1 and FVC measurements. Comparisons are made between the placebo and control groups using unpaired, two-tailed t analysis, and comparisons of patient data at the start of the study to those measurements obtained after 4 weeks of either lidocaine or placebo are made by paired two-tailed t analysis. Symptom scores are summed on a daily basis and a total weekly score is computed by summation of daily scores. Comparisons of symptom scores are made between and within groups for each of the weekly intervals. Dropouts are not replaced in the study. The dropout number is compared between the two groups at the end of the study, and the study week that the patient dropped out in each group isl also compared.

Patient Safety and Risk Reduction:

All subjects receive their first nebulization procedure under observation with recording of before and after nebulization FEV1. As lidocaine is a topical anesthetic and when nebulized results in temporary laryngeal numbness, all subjects are asked to not eat for 15 minutes before and one hour after each nebulization to reduce the risk of aspiration of ingested solids or liquids.

Lidocaine toxicity is related to serum concentration and does not occur until serum concentrations exceed 5–6 µg/ml. It has been found, using a PAR1 II nebulizing device, that nebulization of up to 375 mg over 10 minutes in four normal subjects and four patients with asthma resulted in a serum concentration of >1 µg/ml, namely 1.5 µg/ml, in only one patient out of eight. Others have shown similar results with laryngeal spraying or direct bronchial instillation of lidocaine. Scott, D. B. et al., *Br J Anaesth.* 48:899–902 (1976); Chinn, W. M. et al., *Chest* 71:346–348 (1977).

If subjects develop increasing shortness of breath, sputum volume, or chest tightness, they report to the clinic for an examination and pulmonary function measurement. If their peak flow rate or FEV1 has fallen more than 25% below their personal best recording; they are dropped from the study. Any patients who are thus dropped, or because of increased symptoms or medication intolerance believe that they cannot continue with the study are arbitrarily assigned the highest symptom score of 12 for the final day in which they participated in the study. An examination, spirometry, CBC, and sputum analysis is obtained at the time of dropout. These patients receive antibiotics or other medications as needed for their exacerbation and are monitored at weekly intervals until they have resumed their baseline status. Patients who believe they have contracted a respiratory infection record these symptoms in their diaries and are not dropped unless they have pulmonary function reduction as described above or believe that they cannot continue.

Patients who have long-term tobacco exposure are at risk for upper and lower airway cancer. The larynx and mouth are inspected thoroughly during the examinations, and all patients over the age of 45 receive a CXR if they have not had one in the preceding 12 months.

Any subject who cannot maintain smoking abstinence for the one month study period is dropped from the study.

Results

Figure 4:
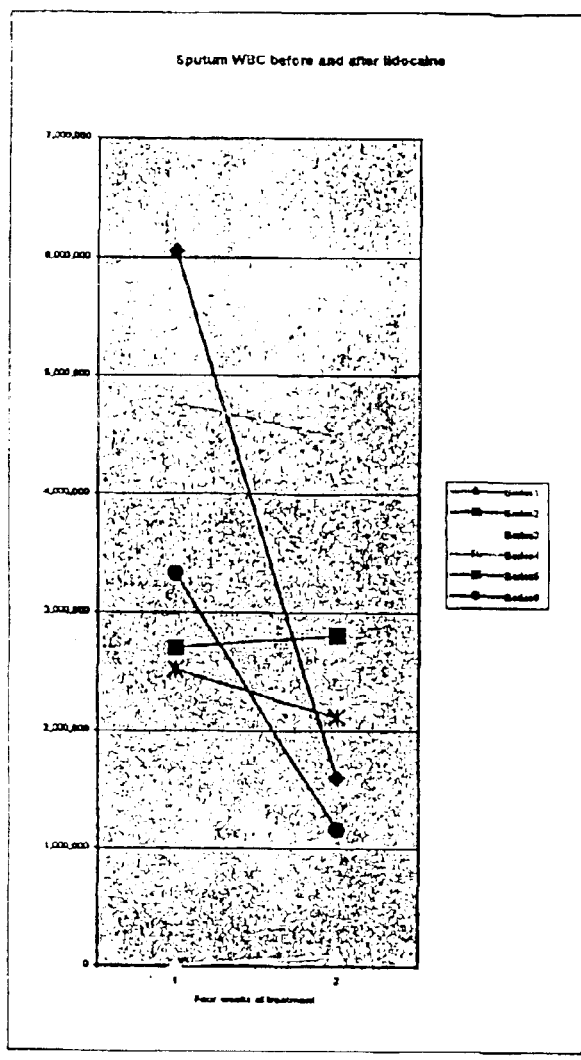
FIG. 4 is a graphical depiction of sputum WBC before and after lidocaine treatment.
Figure 5:
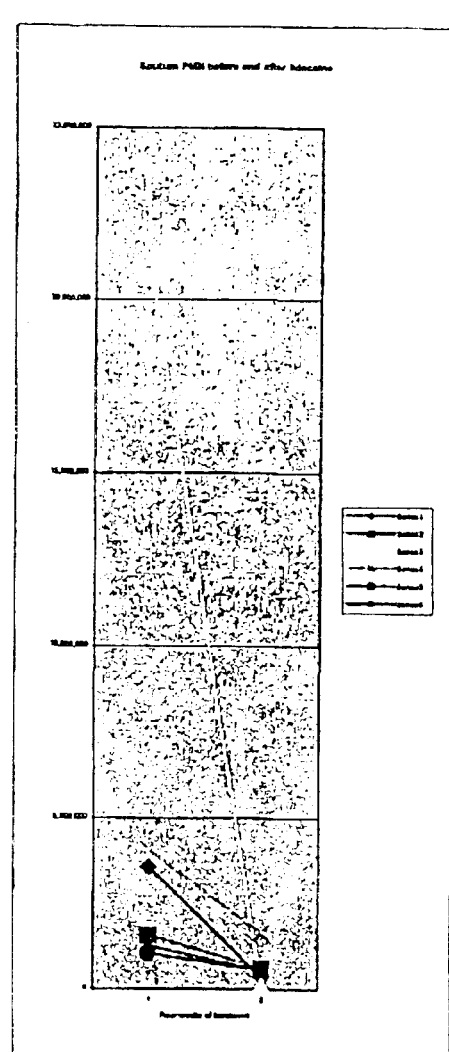
FIG. 5 is a graphical depiction of sputum PMN before and after lidocaine treatment.

Preliminary data have recently been obtained that indicate that nebulized lidocaine is effective in treatment of sputum neutrophilia in patients with chronic protracted post-viral or post-irritant cough. Six such patients are shown in Table 1 and FIGS. 4 and 5. Table 2 provides information regarding normal values. Each showed reduction of sputum neutrophils after four weeks of nebulized lidocaine which coincided with clearing of their cough. These patients had been symptomatic for 8–72 weeks and all had failed to respond to topical glucocorticoids and multiple courses of antibiotics.

TABLE 1

| | wbc before | wbc after | pmn before | pmn after | eos before | eos after |
|---|---|---|---|---|---|---|
| 2 | 6,050,000 | 1,600,000 | 3,569,000 | 352,000 | 484,000 | 96,000 |
| 1 | 2,700,000 | 2,808,000 | 1,566,000 | 617,760 | 12,798 | 2,808 |
| 3 | 34,620,00 | 85,000 | 2,772,000 | 79,900 | 1,384,200 | 0 |
| 4 | 4,760,000 | 4,480,300 | 4,093,400 | 1,612,800 | 0 | 134,400 |
| 5 | 2,512,500 | 2,120,000 | 1,256,250 | 551,200 | 0 | 42,500 |
| 7 | 3,330,000 | 1,160,000 | 1,032,200 | 568,400 | 0 | 0 |

EXAMPLE 4

Lidocaine Effects on the Stimulation and Degranulation of Neutrophils

Neutrophils are white blood cells that provide a line of defense against acute bacterial or fungal infections and are also important in numerous inflammatory conditions. Via degranulation and fusion of such granules with phagosomes, neutrophils destroy invading microorganisms. However, neutrophils concomitantly release granules extracelluarly which can induce tissue damage and amplification of inflammatory response.

Inflammation of neutrophils and their extracellular release of granule proteins are thought to be involved in the pathogenesis of inflammatory lung disorders including COPD, Chronic Bronchitis and CF. Targets of neutrophils include the lung and bronchial epithelium. Previous studies have revealed that the release of $O_2^-$ and serine proteinases (i.e., elastase) affect the integrity of the epithelial layer, decrease the frequency of ciliary beat, increase secretion of mucus, and induce neutrophil-dominated inflammation. Hiemstra, P. S. et al., *European Respiratory Journal* 12:1200 (1998).

Previously, it was discovered that lidocaine exerted a useful effect on patients with severe asthma. In a clinical trial, twenty patients with severe asthma received 100 mg nebulized lidocaine×4 qd. As a result a result of this treatment, seventeen patients were able to discontinue or reduce the use of oral GC by 80%. Furthermore, lidocaine was found to have minimal side effects.

Methods

Neutrophils were isolated in a Percoll gradient to remove PBMC. Red blood cells were lysed and neutrophils were collected from the granulocyte pellet at an average of 91.3% purity.

The extracellular superoxide assay (Cytochrome C method) was performed as follows: 1) The wells of a 96-well plate were blocked with 50 µl of 1% HSA for at least 2 hours at 37° C. 2) The Cytochrome C mix (#C-2506, Sigma, St. Louis, Mo.) was prepared as follows: 2.4 mgs of Cytochrome C was resuspended in 1 mL HBSS/HEPES (pH 7.4).

TABLE 2

Normal Values

| Name Normals | Sex | Age | Amount | WBC (cellx106) | Squamous (cellx106) | PMN % | Lymphocyte % | Eosinophil % | Macrophage | Sqamous % | Ciliated Columnar | Unidentified (cell/100 WBC) |
|---|---|---|---|---|---|---|---|---|---|---|---|---|
| 1 | M | 43 | 3 | 0.49 | 0.46 | 49 | 6 | 1 | 6 | 18 | 16 | |
| 2 | M | 54 | 3 | 1.2 | 0.926 | 15 | 5 | 0 | 5 | 40 | 15 | 20 |
| 3 | F | 35 | 7 | 0.435 | 0.084 | 47 | 22 | 0 | 14 | 9 | 0 | 8 |
| 4 | F | 42 | 5 | 0.108 | 0.104 | 28 | 7 | 0 | 19 | 45 | 1 | |
| 5 | F | 46 | 5 | 0.148 | 0.148 | 32 | 4 | 0 | 11 | 21 | 32 | |
| 6 | M | 52 | 5 | 0.112 | 0.16 | 35 | 18 | 0 | 5 | 36 | 5 | |
| 7 | M | 28 | 5 | 0.048 | 0.5 | 10 | 2 | 0 | 1 | 85 | 2 | |
| 8 | M | 29 | 3 | 1.32 | 0.16 | 40 | 3 | 0 | 17 | 19 | 21 | |
| 9 | M | 40 | 7 | 0.146 | 0.348 | 45 | 3 | 0 | 14 | 33 | 1 | |
| 10 | M | 37 | 5 | 0.082 | 0.44 | 11 | 0 | 0 | 0 | 89 | 0 | 8 |
| 11 | F | 23 | 5 | 0.304 | 0.154 | 19 | 1 | 1 | 14 | 33 | 32 | 36 |
| 12 | M | 33 | 5 | 0.528 | 0.154 | 65 | 7 | 0 | 8 | 17 | 2 | 38 |
| 13 | M | 36 | 3.5 | 1.79 | 0.187 | 61 | 9 | 0 | 22 | 6 | 2 | 19 |
| 14 | F | 61 | 2.5 | 0.543 | 0.297 | 25 | 2 | 5 | 40 | 25 | 3 | 25 |
| 15 | M | 37 | 5 | 0.956 | 0.384 | 46 | 4 | 1 | 6 | 43 | | 5 |
| 16 | F | 48 | 3.5 | 0.126 | 0.06 | 42 | 5 | 0 | 8 | 43 | 2 | 6 |
| 17 | M | 40 | 7 | 0.291 | 0.205 | 30 | 2 | 0 | 16 | 38 | 14 | 7 |
| 18 | F | 32 | 3 | 1.16 | 1.07 | 31 | 4 | 0 | 10 | 47 | 8 | 3 |
| | | | 4.6 | 0.544 | 0.325 | 35.1 | 5.8 | 0.4 | 12 | 35.9 | 9.2 | |
| | | | 1.2 | 0.41 | 0.21 | 13 | 3.8 | 0.7 | 6.7 | 15.8 | 8.8 | |
| | | | | 0.52 | 0.28 | 15.8 | 5.7 | 1.2 | 9.3 | 22.4 | 10.8 | |

One mL of CytoC mix was required for every $0.5 \times 10^6$ cells used in the assay. 3) The blocked cells of the 96 well plate were washed twice with 200 μL saline. 4) 4× stimulus and inhibitor stocks were prepared HBSS/HEPES. The cells were resuspended in CytoC mix to $0.5 \times 10^6$ cells/mL and kept on ice until ready for use. 5) The final volume in all wells was 200 μL: 100 μl cell/CytoC mix suspension per well ($0.05 \times 10^6$ cells/well); 50 μL stimulus (if present) per well and 50 μL inhibitor (if present) per well. If stimulus and/or inhibitor was not required for a well, the volume was made up with HBSS/HEPES so that the total volume in the well was 200 μL. 6) Stimuli, inhibitors and cells were added to the wells in the following order: 1) media filler; 2) inhibitors; 3) cells; and 4) stimuli. 7) The 96 well plate was placed in a ThermoMax plate reader and the $OD_{550}$ was read at 37° C. The plate was read at time 0 and then every 10 minutes for 1 hour, then every 30 minutes for 3 hours. 8) The concentration of superoxide released was calculated by using the following formula to calculate the nmol of Cytochrome C reduced: $19.1*[OD_{550}(time\ x) - OD_{550}(time\ 0)]/0.05$ = nmol Cytochrome C reduced per $1 \times 10^6$ cells = nmol superoxide released per $1 \times 10^6$ cells.

To measure lactoferrin, an ELSIA kit was purchased from Calbiochem (San Diego, Calif.) and the protocols and procedures were followed therein.

Results and Discussion

Figure 6:
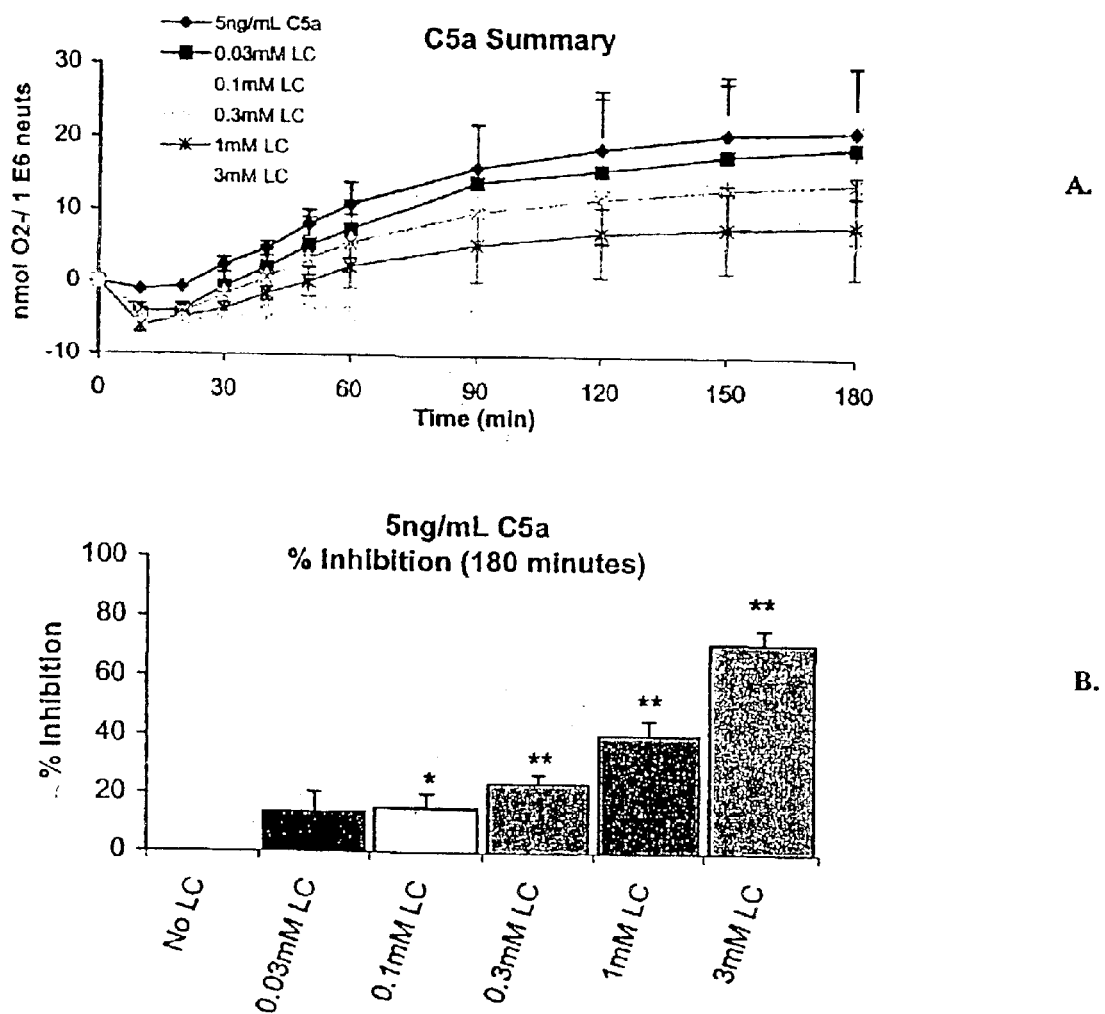
FIGS. 6A and 6B are graphical depictions of the effect of C5a and lidocaine on neutrophil superoxide anion production. The results show that C5a stimulates superoxide anion production. In contrast, lidocaine suppresses the C5a stimulated neutrophils superoxide anion production.

The following stimuli were screened: granulocyte colony stimulating factor (G-CSF); granulocyte macrophage colony stimulating factor (GM-CSF); interferon gamma (γ) (IFN-γ); interleukin 8 (IL-8); tumor necrosis factor α (TNF-α); C5a (component of the complement system); f-met-leu-phe (peptide; fMLP); leukotriene $B_4$ ($LTB_4$); platelet activating factor (PAF); immunoglobulin G (IgG); serum opsonized zymosan (SOZ); and activation of PKC (PMA). C5a, GM-CSF, fMLP, TNF-α, IgG, PAF, SOZ, PMA all stimulated the neutrophils to release extracellular superoxide, while 5 μg/mL G-CSF, 100 ng/mL, 1 ug/mL IFN-γ, 0.5, 1 and 10 ng/mL IL-8 and 100 nM and 1 uM $LTB_4$ did not stimulate the neutrophils to release extracellular superoxide. It was demonstrated that lidocaine inhibits the stimulation of neutrophils in a dose dependent manner by all stimuli with the exception of PMA (summary of C5a stimulation and inhibition by lidocaine is depicted in FIGS. 6A and 6B).

Figure 7:
FIG. 7 is a graphical representation of the effect of lidocaine on lactoferrin release.

When neutrophils begin to invade injured tissue, feedback control of inflammation begins with degranulation of neutrophils and massive release of lactoferrin. The amount of lactoferrin released from neutrophils stimulated with PMA, TNF-α and PAF was measured. It was determined that lidocaine significantly inhibits lactoferrin release in neutrophils that are stimulated with TNF and may have an effect on lactoferrin release in PMA stimulated neutrophils (FIG. 7).

Thus, lidocaine obstructed the stimulation and degranulation of neutrophils.

All publications and patents are herein incorporated by reference to the same extent as if each individual publication or patent application was specifically and individually indicated to be incorporated by reference. Specifically, the literature and patents incorporated by reference in the section on "Topical Anesthetics" are incorporated for their teaching of analogs, salts and derivatives of the anesthetics specifically disclosed herein, which can also be used in the present invention. It will be apparent to one of ordinary skill in the art that many changes and modifications can be made in the invention without departing from the scope of the appended claims.

What is claimed is:

1. A method for treating a neutrophil-associated pulmonary disease selected from chronic obstructive pulmonary disease (COPD), chronic bronchitis (CB), cystic fibrosis, α-1 anti-trypsin deficiency, pulmonary emphysema, adult respiratory distress syndrome, and idiopathic pulmonary fibrosis comprising locally administering to the respiratory tract of an afflicted human an amount of a therapeutic preparation comprising a topical anesthetic effective to counteract the symptoms of the disease, wherein the topical anesthetic is an N-aryl amide or carboxamide.

2. The method of claim 1 wherein the therapeutic preparation is administered in combination with a pharmaceutically acceptable liquid vehicle.

3. The method of claim 1 wherein the therapeutic preparation is administered by spraying or by nebulization.

4. The method of claim 1 wherein the topical anesthetic is administered at a daily dose of about 2.0–15 mg/kg.

5. The method of claim 1 wherein the topical anesthetic is bupivacaine, dibucaine, or an N-arylamide; or a pharmaceutically acceptable salt thereof.

6. The method of claim 5 wherein the topical anesthetic is an N—($C_7$–$C_{22}$)arylamide of an amino-substituted ($C_1$–$C_5$) carboxylic acid or a pharmaceutically acceptable salt thereof.

7. The method of claim 6 wherein the topical anesthetic is an N-[(mono- or di-($C_1$–$C_4$)alkyl)phenyl]amide of an aliphatic ($C_1$–$C_5$)carboxylic acid, wherein said acid is substituted with (R)(R')N—, wherein R is H or ($C_1$–$C_5$)alkyl and R' is ($C_1$–$C_5$)alkyl; or a pharmaceutically acceptable salt thereof.

8. The method of claim 7 wherein the topical anesthetic is lidocaine, prilocaine, etidocaine, or a pharmaceutically acceptable salt thereof.

9. The method of claim 8 wherein the topical anesthetic is lidocaine or lidocaine hydrochloride.

* * * * *